US005568657A

United States Patent [19]
Cordova et al.

[11] Patent Number: 5,568,657
[45] Date of Patent: Oct. 29, 1996

[54] CUT RESISTANT PROTECTIVE GLOVE

[75] Inventors: David S. Cordova, Midlothian; Gene C. Weedon, Richmond; Robert C. W. Hofer, Richmond; Mark B. Boone, Richmond; Kevin M. Kirkland, Richmond, all of Va.; Charles P. Weber, Jr., Monroe, N.C.; Gregory J. LaCasse, Lancaster, Pa.

[73] Assignee: AlliedSignal Inc., Morristown, N.J.

[21] Appl. No.: 405,330

[22] Filed: Mar. 16, 1995

Related U.S. Application Data

[62] Division of Ser. No. 931,126, Aug. 17, 1992, Pat. No. 5,418,977, which is a continuation of Ser. No. 798,983, Nov. 29, 1991, abandoned, which is a continuation of Ser. No. 462,249, Jan. 9, 1990, abandoned.

[51] Int. Cl.⁶ .................................................. A41D 19/00
[52] U.S. Cl. ............................... 2/167; 2/161.7; 2/164
[58] Field of Search ........................... 2/164, 161.7, 167, 2/168, 2.5, 21

[56] References Cited

U.S. PATENT DOCUMENTS

| | | | |
|---|---|---|---|
| 3,883,898 | 5/1975 | Byrnes, Sr. | 2/167 |
| 3,934,062 | 1/1976 | Tillotson et al. | 2/167 X |
| 4,004,295 | 1/1977 | Byrnes, Sr. | 2/161 |
| 4,283,244 | 8/1981 | Hashmi | 2/168 X |
| 4,384,449 | 5/1983 | Byrnes, Sr. et al. | 2/167 X |
| 4,454,611 | 6/1984 | Tschirch et al. | 2/161 R |
| 4,466,151 | 8/1984 | Barch et al. | 2/167 X |
| 4,470,251 | 9/1984 | Bettcher | 66/174 X |
| 4,536,890 | 8/1985 | Barnett et al. | 2/164 |
| 4,651,514 | 5/1987 | Collett . | |
| 4,742,578 | 5/1988 | Seid | 2/2.5 |
| 4,777,789 | 10/1988 | Kolmes et al. | 2/167 X |
| 4,779,290 | 10/1988 | Welch et al. | 2/167 X |
| 4,833,733 | 5/1989 | Welch et al. | 2/167 |
| 4,858,245 | 8/1989 | Sullivan et al. | 2/21 |
| 4,864,661 | 9/1989 | Gimbel | 2/167 |
| 4,886,691 | 12/1989 | Wincklhofer . | |
| 4,975,543 | 12/1990 | Saunders | 57/225 X |
| 5,070,540 | 12/1991 | Bettcher et al. | 2/161 R X |
| 5,087,499 | 2/1992 | Sullivan | 2/169 X |
| 5,119,512 | 6/1992 | Dunbar et al. . | |

FOREIGN PATENT DOCUMENTS

| | | |
|---|---|---|
| 0133205 | 2/1984 | European Pat. Off. . |
| 0168774 | 1/1986 | European Pat. Off. . |
| 2477583 | 9/1981 | France . |
| 3126016 | 1/1983 | Germany . |
| 1194235 | 8/1986 | Japan . |
| 1020351 | 1/1989 | Japan . |
| 2154018 | 6/1990 | Japan . |
| 20845 | 12/1899 | Switzerland ........................ 2/164 |
| 965720 | 8/1964 | United Kingdom . |

OTHER PUBLICATIONS

"New High–strength Fiber Finding Innovative Uses ini Protective Clothing", *Chemical and Engineering News*, vol. 67, No. 41, pp. 23–24 (Oct. 9, 1989).
"Aids Spurs Race for Greater Protection in Surgical Gloves" and Clean, White and Safe, *Kaleidoscope,* Issue 3, vol. III, pp. 2 and 4 (Winter 1988).
Paraderm™ Glove Liners Advertisement.

*Primary Examiner*—John J. Calvert
*Attorney, Agent, or Firm*—Renee J. Rvmarz; Melanie L. Brown

[57] ABSTRACT

A flexible, uncoated glove made from nonmetallic fabric comprising at least one fiber is disclosed. The glove is characterized by either weighing no more than about 30 g or having a thickness of no more than about 1.25 mm (0.05 inch), being cut resistant over some portion thereof by enduring without cutting through at least 5 cycles of an impact cam cut test, having compliance so that the wearer has a high degree of tactility, and having a cut resistance of at least 5 cycles of an impact cam cut test after a disinfectant treatment with sodium hypochlorite. The gloves are particularly useful in the medical field where they provide excellent cut protection and can be disinfected at least once while maintaining an acceptable level of cut resistance. In an alternate embodiment, a similarly characterized glove is made from a layer of fibrous material adhered to a surface of an elastomeric glove without being fully encapsulated thereby. This glove is also particularly useful in the medical field where it provides excellent cut protection.

13 Claims, 1 Drawing Sheet

CUT RESISTANT PROTECTIVE GLOVE

This application is a division of application Ser. No. 07/931,126 filed Aug. 17, 1992 U.S. Pat. No. 5,418,977 which is a continuation of Ser. No. 07/798,983 filed Nov. 29, 1991 (abandoned), which is a continuation of Ser. No. 07/462,249 filed Jan. 9, 1990 (abandoned).

BACKGROUND OF THE INVENTION

1. Field of the Invention

The present invention relates to cut resistant protective gloves and more particularly to an uncoated, ultra-lightweight, cut resistant surgeon's glove which has cut resistance even after disinfectant treatment with sodium hypochlorite.

The gloves of the present invention may be worn alone or in combination with other gloves and therefore, the term "glove" herein is intended to encompass glove liners as well as gloves.

2.1 The Prior Art—Problems Faced

With the onslaught of the AIDS crisis and the spread of various hepatitis infections, the medical community has been searching for new ways to protect themselves from the risk of infection from body fluids. By medical community is meant people who come into contact with these body fluids, e.g., doctors such as surgeons and pathologists, dentists, nurses, hospital technicians, emergency medical technicians, veterinarians, embalmers and other funeral personnel. The fear of AIDS infection by medical professionals has received a great deal of media attention recently, primarily for two reasons: first, AIDS is a contagious disease that nearly always results in death, and second, some medical professionals are leaving their positions due to that fear. NEWSWEEK, Nov. 20, 1989, pp 82-3, Volume CXIV, No. 21. SIXTY MINUTES, Sep. 24, 1989, 7:22 p.m., WCBS/TV & THE CBS TV NETWORK, New York.

Hand protection has become a major priority in order to counter infectious threats from cuts during surgery or whenever hands are exposed simultaneously to body fluids and sharp edges, e.g., emergency medical technicians attending people in automobile accidents involving torn metal or shattered glass. Use of a highly cut resistant glove to fit under, over or between the standard latex medical gloves is highly desirable in such instances due to the latex glove's susceptibility to cuts. Such a glove, however, must provide this cut protection while minimizing problems of retaining dexterity and tactile sensitivity, and of allergenic reactions. Furthermore, since some medical personnel pour Dakin's Solution (5% sodium hypochlorite solution), a known disinfectant for the AIDS virus, inside their gloves to protect themselves in the event that their glove is cut, punctured, or torn during use, such a glove should also have cut resistance after exposure to such a solution.

2.2 The Prior Art—Earlier Attempts at Protection

Some prior efforts for hand protection have used chain mail gloves or other varieties of metal fibers in gloves that, while cut resistant, are stiff and awkward as well as heavy. Heavy gloves produce hand fatigue that may aggravate or cause very uncomfortable conditions such as carpal tunnel syndrome. Lighter weight gloves of cotton, polyester or other textile fibers provide the desired tactile sensitivity but no appreciable protection from cuts; to provide significant cut protection with these materials would require so much fabric that the glove would be practically inflexible due to bulk, and the wearer would have little or no tactile sensitivity.

A surgeon's glove has been developed and is disclosed by U.S. Pat. No. 4,779,290 and division thereof, U.S. Pat. No. 4,833,733, both of which are hereby incorporated by reference. This surgical glove provides tactility on the ventral side and cut protection on the dorsal side. The dorsal side includes a layer of flexible armor material, preferably interwoven fibers of nylon or Kevlar®, embedded in a stretchable air and water impermeable material which is integrally connected to a ventral side which also includes a thin layer of stretchable air and water impermeable material, preferably latex. While this glove could possibly be sterilized for reuse, the manufacturer's test for leaks is not one that a typical hospital/medical facility runs; without such testing, there can be no guarantee that the glove wouldn't have a pinhole or other aperture through which infectious fluids could be transmitted on subsequent use. As a practical matter, therefore, elastomeric coated gloves would be used only once prior to their disposal. Economics favors disposal over sterilization for a standard latex medical glove—when cut resistant materials are incorporated, however, sterilization may be more favorable economically. Consequently, it would be desirable to have a cut resistant glove which could be sterilized as part of a hospital/medical facility's routine without the necessity of retesting the glove for leaks.

It is also known to make cut resistant fabric for protective gloves in the meat cutting industry. For example see U.S. Pat. Nos. 3,883,898, 4,004,295, 4,384,449 and 4,470,251, all of which are hereby incorporated by reference. U.S. Pat. No. 3,883,898 suggests using an aramid fiber such as Kevlar® in lightweight, flexible, cut resistant gloves. The other three patents suggest using a nonmetallic fiber such as Kevlar® in combination with a metallic fiber to form lightweight, flexible, cut resistant gloves. All of the patents suggest that the aramid component of the gloves tolerates the rather high temperatures encountered during laundering and sterilization of the gloves. Furthermore, the weight of the gloves, 56.7 g. (about 2 oz.), is touted as significantly lower than that of the prior art metal mesh gloves, of about 340 to 397 g. (about 12 to 14 oz.), according to U.S. Pat. No. 4,384,449.

European Patent Application 0 118 898, published Sep. 19, 1984, teaches a protective, cut resistant glove which is preferably knitted from yarn having a core of one or more wire strands and a fiber strand, and two wrappings of fiber strands. The knitted glove is at least partially coated in an elastomeric material. The total diameter of the yarn is no greater than 1.27 mm, and while relatively lightweight, the glove shell alone weighs in excess of about 55.3 g.

U.S. Pat. No. 4,651,514, hereby incorporated by reference, teaches a cut resistant glove made from a yarn which comprises a core of monofilament nylon, a first wrap on the core comprising at least one strand of aramid fiber, and a second wrap on the core comprising a strand of nylon. The stated advantage of this yarn over that suggested in, for example, U.S. Pat. No. 4,004,295 is that this yarn is electrically nonconductive. This glove would lose some of its cut resistance after disinfectant treatment with sodium hypochlorite, as is explained further below.

Other prior art of interest is U.S. Pat. No. 4,777,789, hereby incorporated by reference, which also teaches a protective glove.

The present invention overcomes many of the limitations of cut resistant gloves made using the prior art.

SUMMARY OF THE INVENTION

The first embodiment of this invention provides a flexible, uncoated glove made from a nonmetallic fabric comprising at least one fiber, preferably a cut resistant fiber, said glove characterized by: weighing no more than about 30 g, preferably no more than about 25 g, more preferably no more than 20 g, and most preferably weighing from about 8 to 20 g; being cut resistant over some portion thereof, preferably the entire hand portion, by enduring without cutting through at least 5 cycles of an impact cam cut test; having compliance so that the wearer has a high degree of tactility; and having a cut resistance of at least 5 cycles of an impact cam cut test after a disinfectant treatment with sodium hypochlorite, more preferably substantially retaining its original cut resistance after disinfectant treatment with sodium hypochlorite.

In a second embodiment, the present invention provides a flexible, uncoated glove made from a nonmetallic fabric comprising at least one fiber, preferably a cut resistant fiber, said glove characterized by: a thickness of no more than about 1.25 mm (0.05 inch); being cut resistant over some portion thereof by enduring without cutting through at least 5 cycles of an impact cam cut test; having compliance so that the wearer can have a high degree of tactility; and having a cut resistance of at least 5 cycles of an impact cam cut test after a disinfectant treatment with sodium hypochlorite, more preferably substantially retaining its original cut resistance after disinfectant treatment with sodium hypochlorite.

It is preferred that the glove of each of these embodiments is further characterized by: substantially retaining its cut resistance after autoclaving at temperatures of up to about 121.1° C. (250° F.) for at least about 30 minutes; being cut resistant over the entire hand portion; substantially retaining its cut resistance after sterilizing with ethylene oxide; and/or being form fitting.

Most preferably the glove of the present invention is a form fitting, flexible, uncoated, medical glove made from a nonmetallic fabric comprising a high molecular weight polyethylene fiber which is cut resistant, said glove being characterized by: weighing no more than about 50 grams, preferably no more than about 30 g, more preferably no more than about 25 g, most preferably no more than 20 g and from about 8 to 20 g; having a thickness of no more than about 1.25 mm (0.05 inch); being cut resistant over the hand portion thereof by enduring without cutting through at least 5 cycles of an impact cam cut test; having compliance so that the wearer can have a high degree of tactility; and substantially retaining its cut resistance after disinfectant treatment with sodium hypochlorite, after sterilizing with ethylene oxide and after autoclaving at temperatures of up to about 121.1° C. (250° F.) for at least about 30 minutes.

In a third embodiment, the present invention provides a flexible, uncoated glove made from a layer of fibrous material, preferably cut resistant fibrous material, adhered to a surface of a latex glove without being fully encapsulated thereby, said glove characterized by: being cut resistant over some portion thereof by enduring without cutting through at least 5 cycles of an impact cam cut test; and having compliance so that the wearer can have a high degree of tactility. In this embodiment, it is also preferred that the glove be further characterized by having a cut resistance of at least 5 cycles of an impact cam cut test after disinfectant treatment with sodium hypochlorite, and by substantially retaining its cut resistance after sterilizing with ethylene oxide or after autoclaving at temperatures of up to about 121.1° C. (250° F.) for at least about 30 minutes. It is furthermore preferred that the glove of this embodiment be characterized by weighing no more than about 30 g, preferably no more than about 25 g, more preferably no more than 20 g, and most preferably by weighing from about 8 to 20 g.

The gloves of this invention are intended for use in any field and the description herein is not intended to limit this invention to medical end uses but to include any use requiring cut resistance and light weight.

DESCRIPTION OF THE PREFERRED EMBODIMENTS

Figure 1:
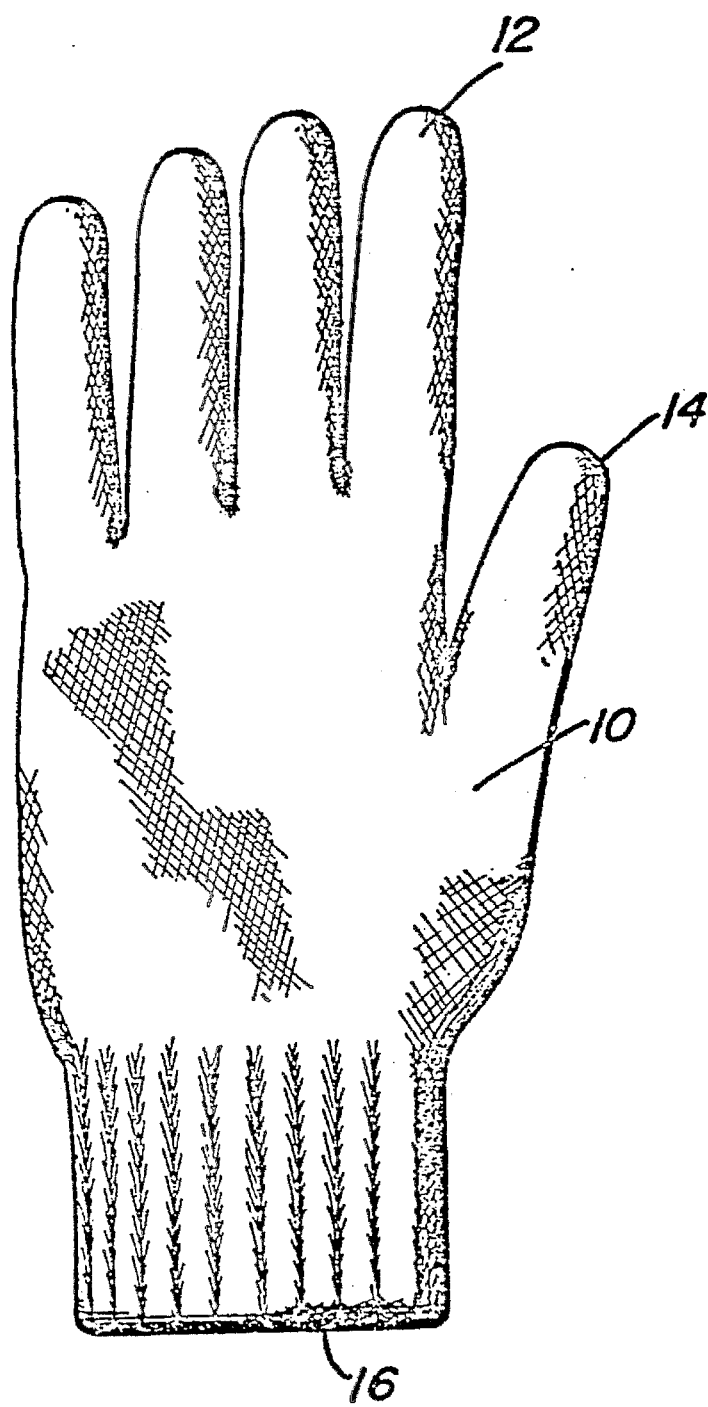
FIG. 1 is a plan view of a cut resistant protective glove of this invention.

Referring to FIG. 1, the protective gloves 10 of the present invention are constructed with conventional finger stalls 12, thumb stall 14, front and back panels, and cuff 16, as are well known in the art. For weight purposes, "glove" is intended to encompass the fabric covering the hand and a cuff of about 3.8 cm (1.5 inches); for all other purposes, "glove" is intended to encompass a cuff or sleeve of any length.

By flexible is meant that the wearer has dexterity approximating that without the glove. By uncoated is meant that the glove itself is not embedded in, coated with or encapsulated by a coating such as an elastomer. By form fitting is meant that the glove snugly fits the hand of the wearer, i.e., conforms to the contours of the hand, including fingers and thumb.

By fiber is meant an elongate body, the length dimension of which is much greater than the transverse dimensions of width and thickness. Accordingly, the term fiber includes monofilament, multifilament, ribbon, strip, staple and other forms of chopped or cut fiber, such as spun staple fibers, and the like, having regular or irregular cross-sections. The fibers may be wrapped with similar or dissimilar fiber, and are processed into fabric by braiding, weaving, felting, fusion bonding, tufting, knitting or the like—the fibers are structurally integrated to form the fabric, and fabric therefore does not include chopped fiber associated only by an elastomer such as latex. Although the fiber may be coated, in the preferred embodiments the fiber is uncoated.

The type of fibers used may vary widely. In the third embodiment, metallic and semi-metallic fibers as are known in the art can be used in combination with natural, inorganic and/or organic fibers. In the other embodiments, nonmetallic fibers are used. The fibers used must form a glove with the claimed characteristics, and therefore, if a polyester or polyamide fiber is used, it must be combined with another fiber in some construction which provides the necessary level of cut protection, as will be shown by the examples which follow. Similarly, although the aramids are listed as useful, applicants have found that uncoated Kevlar aramid staple fiber (spun Kevlar fiber glove) deteriorates after immersion for five minutes in a sodium hypochlorite solution (5%) heated to body temperature (about 30° C.), and it is already known that the breaking tenacity of Kevlar aramid fiber is seriously degraded by repeated laundering with hypochlorite bleach (more dilute solution). With respect to the first two embodiments of this invention, if an aramid staple fiber is primarily responsible for the cut resistance of a glove made therefrom, the aramid staple fiber must be susceptible to some treatment (e.g., coating or overwrapping) that would permit it to form a glove which survives (as well as has the required cut resistance after) a disinfectant treatment with sodium hypochlorite.

With the foregoing in mind, illustrative natural fibers are wool, cotton, silk, flax, linen, ramie. These natural fibers are not normally cut resistant; however, if blended or coated with cut resistant polymer they could be used in this invention. The same is true of some organic fibers and most inorganic fibers.

Illustrative organic fibers are those composed of polyesters, polyamides, polyolefins, aramids (aromatic polyamides), liquid crystalline polymers, polyacrylonitriles, polyvinyl alcohols, and rayons.

Illustrative inorganic fibers for use in the present invention are glass fibers, carbon fibers, ceramic fibers, metal fibers as for example steel, copper, brass, aluminum metal alloys, and the like.

It is preferred that the cut resistant fiber be made from a high molecular weight polyolefin, preferably high molecular weight polyethylene or high molecular weight polypropylene, an aramid, a high molecular weight polyvinyl alcohol, a high molecular weight polyacrylonitrile, liquid crystal polyesters or mixtures or copolymers thereof.

U.S. Pat. No. 4,457,985, hereby incorporated by reference, generally discusses high molecular weight polyethylene and polypropylene fibers. In the case of polyethylene, suitable fibers are those of molecular weight of at least 150,000, preferably at least 400,000, more preferably at least one million and most preferably between two million and five million. Such extended chain polyethylene (ECPE) fibers may be grown in solution as described in U.S. Pat. No. 4,137,394 or U.S. Pat. No. 4,356,138, hereby incorporated by reference, or may be a filament spun from a solution to form a gel structure, as described in German Off. 3 004 699 and GB 2 051 667, and especially described in U.S. Pat. No. 4,551,296, hereby incorporated by reference. As used herein, the term polyethylene shall mean a predominantly linear polyethylene material that may contain minor amounts of chain branching or comonomers not exceeding 5 modifying units per 100 main chain carbon atoms, and that may also contain admixed therewith not more than about 50 weight percent of one or more polymeric additives such as alkene-1-polymers, in particular low density polyethylene, polypropylene or polybutylene, copolymers containing mono-olefins as primary monomers, oxidized polyolefins, graft polyolefin copolymers and polyoxymethylenes, or low molecular weight additives such as lubricants, colorants and the like which are commonly incorporated by reference. Depending upon the formation technique, the draw ratio and temperatures, and other conditions, a variety of properties can be imparted to these fibers. The tenacity of the fibers should be at least 15 g/d, preferably at least 20 g/d, more preferably at least 25 g/d and most preferably at least 28 g/d. Similarly, the tensile modulus of the filaments, as measured by an Instron tensile testing machine, is at least 300 g/d, preferably at least 500 g/d and more preferably at least 1,000 g/d and most preferably at least 1,200 g/d. These highest values for tensile modulus and tenacity are generally obtainable only by employing solution grown or gel fiber processes.

Similarly, highly oriented polypropylene of molecular weight at least 200,000, preferably at least one million and more preferably at least two million, may be used. Such high molecular weight polypropylene may be formed into reasonably well oriented fibers by techniques described in the various references referred to above, and especially by the technique of U.S. Pat. Nos. 4,663,101 and 4,784,820, hereby incorporated by reference, and U.S. patent application Ser. No. 069,684, filed Jul. 6, 1987 (see published application WO 89 00213). Since polypropylene is a much less crystalline material than polyethylene and contains pendant methyl groups, tenacity values achievable with polypropylene are generally substantially lower than the corresponding values for polyethylene. Accordingly, a suitable tenacity is at least about 8 g/d, with a preferred tenacity being at least about 11 g/d. The tensile modulus for polypropylene is at least about 160 g/d, preferably at least about 200 g/d.

In the case of aramid fibers, suitable aramid filaments formed principally from aromatic polyamide are described in U.S. Pat. No. 3,671,542, which is hereby incorporated by reference. Preferred aramid fiber will have a tenacity of at least about 20 g/d, a tensile modulus of at least about 400 g/d and an energy-to-break at least about 8 joules/g, and particularly preferred aramid fiber will have a tenacity of at least about 20 g/d, a modulus of at least about 480 g/d and an energy-to-break of at least about 20 joules/g. Most preferred aramid fiber will have a tenacity of at least about 20 g/d, a modulus of at least about 900 g/d and an energy-to-break of at least about 30 joules/g. For example, poly(p-phenylene terephthalamide) filaments produced commercially by Dupont Corporation under the trade name of Kevlar® 29, 49, 129 and 149 and having moderately high moduli and tenacity values are particularly useful.

High molecular weight polyvinyl alcohol fibers having high tensile modulus are described in U.S. Pat. No. 4,440,711, hereby incorporated by reference. Particularly useful PV-OH fiber should have a modulus of at least about 300 g/d, a tenacity of at least about 7 g/d (preferably at least about 10 g/d, more preferably about 14 g/d, and most preferably at least about 17 g/d), and an energy-to-break of at least about 8 joules/g. PV-OH fiber having a weight average molecular weight of at least about 200,000, a tenacity of at least about 10 g/d, a modulus of at least about 300 g/d, and an energy to break of about 8 joules/g is more useful. PV-OH fiber having such properties can be produced, for example, by the process disclosed in U.S. Pat. No. 4,599,267.

In the case of polyacrylonitrile (PAN), PAN fibers for use in the present invention are of molecular weight of at least about 400,000. Particularly useful PAN fibers should have a tenacity of at least about 10 g/d and an energy-to-break of at least about 8 joules/g. PAN fibers having a molecular weight of at least about 400,000, a tenacity of at least about 15 to about 20 g/d and an energy-to-break of at least about 8 joule/g are most useful. Such fibers are disclosed, for example, in U.S. Pat. No. 4,535,027.

Useful liquid crystalline polymers include lyrotropic liquid crystalline polymers which include polypeptides such as poly γ-benzyl L-glutamate and the like; aromatic polyamides such as poly(1,4-benzamide), poly(chloro-1-4-phenylene terephthalamide), poly(1,4-phenylene fumaramide), poly(chloro-1,4-phenylene fumaramide), poly(4,4'-benzanilide trans, trans-muconamide), poly(1,4-phenylene mesaconamide), poly(1,4-phenylene) (trans-1,4-cyclohexylene amide), poly(chloro-1,4-phenylene) (trans-1,4-cyclohexylene amide), poly(1,4-phenylene 1,4-dimethyl-trans-1,4-cyclohexylene amide), poly(1,4-phenylene 2.5-pyridine amide), poly(chloro- 1,4-phenylene 2.5-pyridine amide), poly(3,3'-dimethyl-4,4'-biphenylene 2.5 pyridine amide), poly(1,4-phenylene 4,4'-stilbene amide), poly(chloro-1,4-phenylene 4,4'-stilbene amide), poly(1,4-phenylene 4,4'-azobenzene amide), poly(4,4'-azobenzene 4,4'-azobenzene amide), poly(1,4-phenylene 4,4'-azoxybenzene amide), poly(4,4'-azobenzene 4,4'-azoxybenzene amide), poly(1,4-cyclohexylene 4,4'-azobenzene amide), poly(4,4'-azobenzene terephthal amide), poly(3,8-phenanthridinone terephthal amide), poly(4,4'-biphenylene terephthal amide), poly(4,4'-biphenylene 4,4'-bibenzo amide), poly(1,4-phenylene 4,4'-bibenzo amide), poly(1,4-phenylene 4,4'- terephenylene amide), poly(1,4-phenylene 2,6-naphthal amide), poly(1,5-naphthalene terephthal amide), poly(3,3'-dimethyl-4,4-biphenylene terephthal amide), poly(3,3'-dimethoxy-4,4'-biphenylene terephthal amide), poly(3,3'-dimethoxy-4,4-biphenylene 4,4'-bibenzo amide) and the like; polyoxamides such as those derived from 2,2'-dimethyl-4,4'-diamino biphenyl and chloro- 1,4-phenylene diamine; polyhydrazides such as poly chloroterephthalic hydrazide, 2,5-pyridine dicarboxylic acid hydrazide) poly-(terephthalic hydrazide), poly(terephthalic-chlorotereph-thalic hydrazide) and the like; poly(amidehydrazides) such as poly(terephthaloyl 1,4 aminobenzhydrazide) and those prepared from 4-aminobenzhydrazide, oxalic dihydrazide, terephthalic dihydrazide and para-aromatic diacid chlorides; polyesters such as those of the compositions include poly-(oxy-trans-1,4-cyclohexyleneoxycarbonyl-trans- 1,4-cyclohexylenecarbonyl-b-oxy- 1,4-phenyl-eneoxyteraphthaloyl) and poly(oxy-cis-1,4-cyclohexyleneoxycarbonyl-trans- 1,4-cyclohexylenecarbonyl-b-oxy- 1,4-phenyleneoxyterephthaloyl) in methylene chloride-o-cresol poly(oxy-trans-1,4-cyclohexylene oxycarbonyl-trans- 1,4-cyclohexylenecarbonyl-b-oxy-(2-methyl-1,4-phenylene)oxy-terephthaloyl) in 1,1,2,2-tetrachloroethane-o-chlorophenolphenol (60:25:15 vol/vol/vol), poly[oxy-trans-1,4-cyclohexyleneoxycarbonyl-trans- 1,4-cyclohexylenecarbonyl-b-oxy( 2-methyl-1,3-phenylene)oxy-terephthaloyl] in o-chlorophenol and the like; polyazomethines such as those prepared from 4,4'-diaminobenzanilide and terephthalaldehyde, methyl-1,4-phenylenediamine and terephthalaldehyde and the like; polyisocyanides such as poly( -phenyl ethyl isocyanide), poly(n-octyl isocyanide) and the like; polyisocyanates such as poly(n-alkyl isocyanates) as for example poly(n-butyl isocyanate), poly(n-hexyl isocyanate) and the like; lyrotropic crystalline polymers with heterocyclic units such as poly(1,4-phenylene-2,6-benzobisthiazole) (PBT), poly(1,4-phenylene-2,6-benzobisoxazole) (PBO), poly(1,4-phenylene- 1,3,4-oxadiazole), poly(1,4-phenylene-2,6-benzobisimidazole), poly[2,5(6)-benzimidazole] (AB-PBI), poly[2,6-(1,4-phenylene-4-phenylquinoline] poly[1,1'-(4,4'-biphenylene)-6,6'-bis(4-phenylquinoline)] and the like; polyorganophosphazines such as polyphosphazine, poly-bisphenoxyphosphazine, poly[bis(2,2,2' trifluoroethylene) phosphazine] and the like; metal polymers such as those derived by condensation of trans-bis(tri-n-butylphosphine-)platinum dichloride with a bisacetylene or trans-bis(tri-n-butylphosphine)bis(1,4-butadinynyl)platinum and similar combinations in the presence of cuprous iodine and an amide; cellulose and cellulose derivatives such as esters of cellulose as for example triacetate cellulose, acetate cellulose, acetate-butyrate cellulose, nitrate cellulose, and sulfate cellulose, ethers of cellulose as for example, ethyl ether cellulose, hydroxymethyl ether cellulose, hydroxypropyl ether cellulose, carboxymethyl ether cellulose, ethyl hydroxyethyl ether cellulose, cyanoethylethyl ether cellulose, ether-esters of cellulose as for example acetoxyethyl ether cellulose and benzoyloxypropyl ether cellulose, and urethane cellulose as for example phenyl urethane cellulose; thermotropic liquid crystalline polymers such as celluloses and their derivatives as for example hydroxypropyl cellulose, ethyl cellulose propionoxypropyl cellulose; thermotropic copolyesters as for example copolymers of 6-hydroxy-2-naphthoic acid and p-hydroxy benzoic acid, copolymers of 6-hydroxy- 2-naphthoic acid, terephthalic acid and hydroquinone and copolymers of poly(ethylene terephthalate) and p-hydroxybenzoic acid; and thermotropic polyamides and thermotropic copoly(amide-esters).

The impact cam cut test is performed using the method and BETATEC™ testing apparatus of U.S. Pat. No. 4,864,852, hereby incorporated by reference. The test involves repeatedly contacting a sample with a sharp edge until the sample is penetrated by the cutting edge. The higher the number of cutting cycles (contacts) required to penetrate the sample, the higher the reported cut resistance of the sample. During testing, the following conditions were used, unless otherwise specified: 90 grams cutting weight, mandrel speed of 50 rpm, rotating steel mandrel diameter of 19 mm, cutting blade drop height of about 8.9 mm (0.35 inch), use of a single-edged industrial razor blade (Red Devil brand) for cutting, cutting arm distance from pivot point to center of blade being about 15.2 cm (about 6 inches). The slicing cam cut test was performed using the method and testing apparatus of U.S. Pat. No. 4,864,852, with the following testing conditions: 45 g cutting weight, mandrel speed of 50 rpm, rotating steel mandrel diameter of 19 mm, cutting blade drop height of 0 mm, use of a single-edged industrial razor blade (Red Devil brand) for cutting, cutting arm distance from pivot point to center of blade being about 15.2 cm (about 6 inches). The slicing cam cut test allows for a cutting edge to be pulled across a sample at a constant load, while the impact cam cut test allows for a cutting edge to abruptly impact a sample; the impact cam cut test is therefore a more onerous test. The gloves were cut tested after cutting fingers from the gloves and mounting the finger on the tester mandrel. The fingers were held on the mandrel with a band clamp placed over the cut end of the fingers.

The level of cut resistance required of the gloves of the present invention is at least 5 cycles of the impact cam cut test. The gloves of the first two embodiments must also have this minimum level of cut resistance after a disinfectant treatment with sodium hypochlorite. It is even more preferred that the gloves substantially retain their cut resistance, which may be higher than the minimum 5 cycles, after one or more disinfectant treatments with sodium hypochlorite. By substantially retain their cut resistance is meant that the gloves lose no more than a statistically insignificant amount of cut resistance.

By disinfectant treatment with sodium hypochlorite is meant immersion in a sodium hypochlorite solution (5%) at about 30° C. for about 5 minutes. If the glove does not disintegrate, it is dried for about 5 minutes in an oven at about 37.8° C. (about 100° F.) and subsequently is tested for cut resistance by cutting a finger from the glove, mounting it on the Betatec tester mandrel, and testing as previously described.

Ethylene oxide sterilization (12% ETO/88% Freon) is carried out under the following common hospital sterilization conditions: temperature of about 54.4° C. (130° F.); humidity level of about 80–100%; maximum pressure of about 21 psi (about $1.5\times10^4$ kg/m$^2$); sterilent concentration of 650 mg/l; and an exposure time of about 105 minutes. Aeration of eight (8) hours minimum in a mechanical aerator at about 48.9°–60° C. (120°–140° F.), 30 to 80 air exchanges/hour. The sterilized glove is tested for cut resistance by cutting a finger from the glove, mounting it on the Betatec tester mandrel, and testing as previously described.

Autoclave sterilization (steam) is carried out at a temperature of 121.1° C. (250° F.) for a cycle time of 30 minutes in the examples which follow. The sterilized glove is tested for cut resistance by cutting a finger from the glove, mounting it on the Betatec tester mandrel, and testing as previously described.

Thickness is measured with an Ames Thickness Gauge #252, commercially available from B. C. Ames Company, and marked with U.S. Pat. No. 2,608,947, hereby incorporated by reference.

The uncoated gloves of the first and second embodiments of the invention can be formed by the cut and sew technique, by knitting or by any other technique known in the art. Knitting is the most preferred method. The uncoated gloves of the present invention are preferably made form fitting by incorporating an elastomeric fiber, such as Spandex® or Lycra®, into the fabric The elastomeric fiber is used as a core yarn and the cut resistant fiber is then over wrapped. In this manner, a fewer number of glove sizes can be manufactured since the elastomeric fiber will allow a certain overlap in sizing.

It is preferred, as shown by all of the uncoated glove examples of the present invention, that the cut resistant portion of the glove be coextensive with the hand portion of the glove, more preferably coextensive with the entire glove, including the cuff. With knitting machine stripers, however, it is possible to provide cut protection in target stripes of the uncoated glove, for instance, in the fingers and thumb. The present invention is intended to cover this.

For surgical purposes, the uncoated glove of the present invention is worn over an inner surgical latex glove to protect it from cuts. An outer surgical latex glove is worn over the uncoated glove to enhance tactility. As noted previously, the yarns utilized can be spun or continuous filament yarns or composite yarns. If the yarn is of the continuous filament type, the total denier may range from about 50 to 2000, more preferably from about 100 to 1200. If the yarn is of the spun type, then the denier per filament may range from about 0.5 to about 15, more preferably from about 1 to 10.

In the third embodiment of the invention, the uncoated glove is made from a layer of fibrous material adhered to a surface of an elastomeric glove without being fully encapsulated thereby. By way of example, elastomers from which the glove can be made include latex, natural rubber, nitrile rubber, and vinyl plastisols; latex is preferred. There are several ways of making the glove of this embodiment. For example, a latex surgical glove can be turned inside out and dipped into a flexible adhesive and then into a fluidized bed of cut fibers. After the adhesive has cured, the glove is turned right side out. The fibrous lining provides cut resistance to the glove. Obviously, the cut fibers could be adhered to the outer surface of the glove in addition to the inner surface or as an alternate thereto. Similarly, the glove could be made by dipping a hand shaped mold into a flexible adhesive and then into a fluidized bed of cut fibers. The adhesive is then allowed to cure. Illustrative of flexible adhesives which can be used are those which are acrylic based, such as the Rhoplex HA and TR types, polyethylene based, such as the George A. Goulston Discosoft series, and Eastman WD Size, a polyester based material, with the latter being preferred. The fibers are as previously described, with cut high molecular weight polyolefin, especially polyethylene, being most preferred. Poly-(p-phenylene terephthalamide) is another useful fibrous material for this embodiment. Alternatively, the fibrous material can be flocked to the elastomeric surface to increase the cut resistance of the glove.

EXAMPLES 1–14

The construction, weight, thickness and cut resistance of gloves for Examples 1–14 are set forth in Tables 1 and 2.

The gloves of Examples 1–5, and 9 were knit using a 13 gauge Shima Seiki glove knitting machine and the knitting parameters set forth in Table 2. The gloves of Examples 10–14 were knit using a 7 gauge Shima Seiki glove knitting machine and the knitting parameters set forth in Table 2. The cotton glove of Comparative Example 6 was the Protek Cotton Glove, commercially available from Protek Inc., and the leather glove of Comparative Example 8 was a pigskin safety glove, commercially available from Stauffer Mfg. Co. of Red Hill, Pa. None of the gloves was coated, and with the exception of the leather glove of Comparative Example 8, all of the gloves had a cuff which was made elastic by incorporation of a Spandex® fiber.

In Example 9, elastomeric threads of 70 denier, type 126 LYCRA®, commercially available from DuPont Corporation, were overwrapped with a 375 denier/60 filament SPECTRA® 1000 fiber, the Lycra fiber forming about 10 weight percent of the yarn, and knit into a glove having improved fit.

In Comparative Example 10, a core fiber comprising glass fiber ECG 75 1/0, 595 denier/204 filaments, commercially available from Owens Corning Fiberglas, and SPECTRA® 1000, 650 denier/120 filaments, was overwrapped with counter opposing helixes of SPECTRA® 1000, 650 denier/120 filaments yarn. The weight percents were, respectively, 21, 19, 27, and 33.

In Example 11, a core fiber comprising glass fiber ECG 75 1/0, 595 denier/204 filaments, commercially available from Owens Corning Fiberglas, and nylon fiber 840 denier/70 filaments, commercially available from Allied-Signal Corporation, was overwrapped with counter opposing helixes of the same nylon fiber. The weight percents were, respectively, 15, 17, 32, and 36.

In Comparative Example 12, a core fiber comprising glass fiber ECG 75 1/0, 595 denier/204 filaments, commercially available from Owens Corning Fiberglas, and polyester fiber 500 denier/70 filaments, commercially available from Allied-Signal Corporation, was overwrapped with counter opposing helixes of the same polyester fiber. The weight percents were, respectively, 26, 17, 28 and 29.

In Example 13, a latex coating was used to encapsulate a glass/extended chain polyethylene fiber. A ECD 900 1/0 glass fiber of about 50 denier/102 filaments in combination with a 185 denier/30 filaments SPECTRA® 1000 yarn were coated with an oil filled latex by Texom Corporation. Final yarn denier was 1017. The weight % latex was about 65.6%.

In Example 14, the glass core ECG 150 1/0 (298 denier/204 filaments) was coated with a latex (75% by weight) and then wrapped with counter opposing helixes of SPECTRA® 1000, 650 denier/120 filaments. The weight percents were, respectively, 33, 33 and 34. This yarn was knitted using the parameters set forth in Table 3 to form a glove. Data is presented in Table 1.

In Examples 1–9, the cut test data represents the average of at least 9 tests. In Examples 10–14 only 1 test was performed.

EXAMPLES 15–16

In Examples 15 and 16, fingers (58 courses or about 2.5 inches long) of fabric were knit using a 13 gauge Shima Seiki glove knitting machine and the knitting parameters set forth in Table 2. These glove fingers were cut tested as previously described. The cut test data for Example 15 represents the average of 6 tests, while the data for Example 16 represents the average of 3 tests.

In Example 15, a core of glass ECG 900 1/0, 50 denier/102 filaments, and an extended chain polyethylene fiber SPECTRA® 1000, 205 denier/60 filaments, was overwrapped with 1 helix of SPECTRA® 1000, 205 denier/60 filaments, to form the yarn. Data is presented in Table 1.

In Example 16, a core of glass ECG 450 1/0, 99 denier/204 filaments, and an extended chain polyethylene fiber SPECTRA® 1000, 375 denier/60 filaments, was overwrapped with 1 helix of SPECTRA® 1000, 375 denier/60 filaments, to form the yarn. Data is presented in Table 1.

EXAMPLES 17–23

In this set of examples, the cut resistance of autoclaved gloves using the slicing cam cut test was measured. Data is presented in Table 3. Elastomeric threads of 70 denier type 126 LYCRA®, commercially available from DuPont Corporation, were overwrapped with a 375 denier/60 filament SPECTRA® 1000 fiber, the Lycra fiber forming about 10 weight percent of the yarn, and knit into gloves weighing about 13 g using a 13 gauge Shima Seiki glove knitting machine and knitting parameters similar to those for Example 9.

In Example 17 (control), the slicing cam cut resistance of 57 gloves was measured, and with reference to Table 3, it can be seen that the mean slicing cam cycles was 32 with a standard deviation of 11 and a range of 57.

A group of 54 gloves was steam autoclaved according to the procedure previously set forth for a 30 minute cycle, after which 9 gloves were removed and tested for slicing cam cut resistance. That data is presented in Table 3 as Example 18. The remaining 45 gloves were steam autoclaved for two additional 30 minute cycles, after which 9 gloves were removed and tested for slicing cam cut resistance. That data is presented in Table 3 as Example 19. The remaining 36 gloves were steam autoclaved for three additional 30 minute cycles, after which 9 gloves were removed and tested for slicing cam cut resistance. That data is presented in Table 3 as Example 20. This process was continued until all of the gloves were tested, the last 9 gloves (Example 23) being exposed to 24 thirty minute cycles. The same finger was tested for each glove.

It was found that the autoclaving process did not adversely affect the slicing cam cut resistance of the glove. Any loss in cut resistance was statistically insignificant. It is believed that the same would hold true for the impact cam cut resistance of the glove.

EXAMPLES 24–29

In this set of examples, the cut resistance of ethylene oxide sterilized gloves using the slicing cam cut test was measured. Data is presented in Table 4. Fifty-four more gloves were made as in Examples 17–23 for testing. Example 17 is deemed the control for this group of examples as well.

As in Examples 18–23, these gloves were exposed to from 1 to 24 cycles of ethylene oxide sterilization, with nine gloves being removed and slicing cam cut tested after 1, 3, 6, 9, 12 and 24 cycles. The mean values obtained are set forth in Table 4 as Examples 24–29, respectively.

It was found that sterilization with ethylene oxide did not adversely affect the slicing cam cut resistance of the glove. Any loss in cut resistance was statistically insignificant. It is believed that the same would hold true for the impact cam cut resistance of the glove.

EXAMPLES 30–39

In this group of examples, gloves were made and tested for impact cam cut resistance after disinfectant treatment with sodium hypochlorite. Glove knitting parameters are set forth in Table 6 and other information is set forth in Table 5. These gloves were rinsed in water after fabrication to remove any finish on the yarn. The gloves were impact cam cut tested and the data recorded (see Table 5) as a control for each type of glove fabrication. The gloves were then immersed in a solution of sodium hypochlorite (5%) at about 30° C. for five minutes. The gloves were removed, rinsed in water, and then dried in an oven for about 5 minutes at about 37.8° C. (about 100° F.). The gloves were impact cam cut tested again and the data recorded (see Table 5) for comparison with the control. There were nine gloves made for each type of fabrication, and the data presented represents the average of 9 samples.

In Examples 30 and 31, the gloves were made from nylon, 420 denier/64 filaments, ¾ Z twist. In Examples 32 and 33, the gloves were made from polyester, 500 denier/70 filaments, zero twist. In Examples 34 and 35, the gloves were made from Kevlar® 29, 400 denier/160 filaments continuous filament. In Examples 36 and 37, the gloves were made from Spectra® 1000, 400 denier/120 filaments. In Examples 38 and 39, the gloves were made from elastomeric threads of 70 denier, type 126 LYCRA®, commercially available from DuPont Corporation, overwrapped with a 375 denier/60 filament SPECTRA® 1000 fiber, the Lycra fiber forming about 10 weight percent of the yarn. The knitting parameters for these gloves are set forth in Table 6. A 13 gauge Shima Seiki knitting machine was used.

EXAMPLE 40 (COMPARATIVE)

The thumb and three fingers of a lightweight (about 15.6 g) glove about 1.15 mm/0.046 inches thick and made from an elastomeric fiber overwrapped with spun (staple) Kevlar® fiber were placed in a sodium hypochlorite solution (5%) at about 30° C. for five minutes. At the end of five minutes, the thumb and fingers could not be tested since they had split apart.

DISCUSSION

The best mode of the first two embodiments of the present invention is deemed to be the gloves of Examples 17–29 (Lycra overwrapped with Spectra) or a glove consisting essentially of 100% Spectra 1000 yarn. The base polymer used in manufacturing the Spectra® extended chain polyethylene fibers, high molecular weight polyethylene, provides a chemically resistant, chemically inert fiber. The solution spinning process for making the extended chain structures in the fiber, however, further enhances this chemical resistance, and surprisingly, provides a stable polyethylene fiber which can be steam autoclaved by normal medical procedures at 121.1° to 132.2° C. (250°–270° F.) or treated with ethylene oxide without a loss in the cut resistant properties. Even sodium hypochlorite (5%), a known disinfectant for the AIDS virus which is frequently used to treat the inside of latex gloves does not attack the extended chain polyethylene fiber. By contrast staple aramid fibers which are also highly cut resistant are severely weakened in minutes at 30° C. in sodium hypochlorite. The nature and structure of extended chain polyethylene fibers also prevents the undesirable absorption of blood and other body fluids into the fibers. Without special surface treatments cotton, nylon, or aramids would be more prone to the absorption and retention of such materials thereby interfering with repeated uses.

In terms of the structural integrity of hybrid, composite yarns, extended chain polyethylene yarns have a distinct advantage as overwraps due to the "dead bend" behavior of such yarns. This "dead bend" phenomenon is noted whenever the fibers are tightly wound about a small radius of curvature such as a central core fiber or wire core. Once wound about a core, the fibers will remain tightly wound even when the winding tension is removed and is indicative of a permanent deformation. If cut, the extended chain polyethylene fibers will tend to remain essentially in place thus continuing to provide protection for the core. By contrast, other high modulus fibers, such as aramids, tend to splay out when cut, particularly if they are tightly wound about a core. The value of this "dead bend" also is important in the case of a metal wire core since this tight winding minimizes kinking of the wire during knitting and so thereby reduces the chance of a kink puncturing a latex glove.

Thus, through the use of this best mode, one can manufacture a thin, lightweight, formfitting glove having a high degree of cut resistance and a high degree of flexibility and chemical resistance.

EXAMPLE 41—THIRD EMBODIMENT

A latex surgical glove, such as is commercially available from Baxter/American Hospital, is stretched on a hand form and then dipped into a 47% water dispersion of Eastman WD Size, commercially available from Eastman Chemical Products, Inc., to give a uniform coating on the surface of the glove. It is then dipped, while still wet, into an electrostatically dispersed fluidized bed of cut SPECTRA® 900 fibers which are 3.1 mm (⅛ inch) long and have a denier per filament of about 10. The cut fibers adhere to the wet surface on withdrawal. The coated form is then air dried at 110° C. for ten minutes and the glove is removed from the form. Removal turns the glove inside out, so that the fibrous material lines the interior of the glove. The glove weighs no more than 20 g. Impact cam cut resistance is expected to be 20 cycles. The glove has a high degree of compliance and substantially retains its cut resistance after disinfectant treatment with sodium hypochlorite, after autoclaving at temperatures of up to about 126.7° C. (260° F.) for at least about 30 minutes, and after sterilizing with ethylene oxide.

TABLE 1

| Ex. | Fiber | Denier/Filaments | Wt. (g) | Thickness mm/Inches | Cut Slicing | Resistance Impact |
|---|---|---|---|---|---|---|
| 1 | Spectra ® 900[1] | 650/60 | 16.5 | 1.00/0.040 | 184 | 35 |
| 2 | Spectra ® 900 | 1200/120 | 14.4 | 1.00/0.040 | 208 | 25 |
| 3 | Spectra ® 1000[1] | 185/30 | 17.3 | 0.68/0.027 | 64 | 30 |
| 4 | Spectra ® 1000 | 375/60 | 9.4 | 0.48/0.019 | 61 | 33 |
| 5 | Spectra ® 1000 | 650/120 | 13.0 | 0.78/0.031 | 158 | 20 |
| 6* | Cotton[2] | — | 21.0 | 1.08/0.043 | 499 | 2 |
| 7* | Nylon | 840/70 | 12.8 | 1.10/0.044 | 83 | 1 |
| 8* | Leather | — | 60.0 | 1.10/0.044 | 2 | 1 |
| 9 | Spectra ® 1000/Lycra | 375/60 70/— | 14.3 | 1.10/0.044 | 35 | 8 |
| 10* | Glass/Spectra ® 1000 | — | 36.0 | 1.50/0.060 | 50K[3] | 637 |
| 11 | Glass/Nylon | — | 47.1 | 1.05/0.042 | 50K[3] | 83 |
| 12* | Glass/Polyester | — | 32.4 | 1.13/0.045 | 50K[3] | 3 |
| 13 | Glass/Spectra ® 1000/Latex | — | 29.8 | 0.85/0.034 | 50K[3] | 30 |
| 14 | Glass/Latex/Spectra ® 1000 | — | 40.0 | 1.15/0.046 | 50K[3] | 73 |
| 15 | Glass/Spectra ® 1000 | N/A | N/A | 0.58/0.023 | 13,898 | 19 |
| 16 | Glass/Spectra ® 1000 | N/A | N/A | 1.25/0.050 | 50K[3] | 126 |

*Comparative
[1]High strength, ultrahigh molecular weight polyethylene commercially available from Allied-Signal Inc.
[2]English Cotton Count −5.5.
[3]Stopped test after 50,000 cycles (K = 1,000 cycles).

TABLE 2

| | GLOVE KNITTING PARAMETERS | | | | | | | | | | | | | | | |
|---|---|---|---|---|---|---|---|---|---|---|---|---|---|---|---|---|
| | LITTLE | | RING | | MIDDLE | | INDEX | | PALM | | THUMB | | HELL | | CUFF | ENDS PER |
| EX. | C | W | C | W | C | W | C | W | C | W | C | W | C | W | C | W | NEEDLES |
| 1 | 40 | 17 | 40 | 21 | 48 | 21 | 40 | 22 | 30 | 66 | 36 | 17 | 12 | 70 | 20 | 79 | 2 |
| 2 | 40 | 17 | 40 | 21 | 48 | 21 | 40 | 22 | 30 | 66 | 36 | 17 | 32 | 70 | 20 | 79 | 1 |
| 3 | 62 | 17 | 81 | 21 | 86 | 21 | 66 | 22 | 54 | 66 | 65 | 17 | 65 | 70 | 45 | 79 | 3 |
| 4 | 44 | 17 | 62 | 21 | 72 | 21 | 62 | 22 | 36 | 66 | 48 | 17 | 46 | 70 | 46 | 79 | 2 |
| 5 | 60 | 17 | 68 | 21 | 74 | 21 | 68 | 22 | 46 | 66 | 52 | 17 | 48 | 70 | 46 | 79 | 1 |
| 6 | | | | | | | Not Applicable | | | | | | | | | | |

TABLE 2-continued

GLOVE KNITTING PARAMETERS

| EX. | LITTLE C | W | RING C | W | MIDDLE C | W | INDEX C | W | PALM C | W | THUMB C | W | HELL C | W | CUFF C | W | ENDS PER NEEDLES |
|---|---|---|---|---|---|---|---|---|---|---|---|---|---|---|---|---|---|
| 7 | 47 | 17 | 66 | 21 | 76 | 21 | 63 | 22 | 42 | 66 | 56 | 17 | 49 | 70 | 65 | 79 | 2 |
| 8 | | | | | | | Not Applicable | | | | | | | | | | |
| 9 | 63 | 17 | 77 | 21 | 84 | 21 | 81 | 22 | 46 | 66 | 70 | 17 | 71 | 70 | 55 | 79 | 1 |
| 10 | 28 | 10 | 34 | 11 | 39 | 11 | 32 | 11 | 22 | 71 | 26 | 20 | 26 | 97 | 24 | 97 | 1 |
| 11 | 26 | 10 | 34 | 11 | 40 | 11 | 32 | 11 | 22 | 71 | 26 | 20 | 26 | 97 | 24 | 97 | 1 |
| 12 | 26 | 10 | 34 | 11 | 40 | 11 | 32 | 11 | 22 | 71 | 26 | 20 | 26 | 97 | 24 | 97 | 1 |
| 13 | 59 | 10 | 67 | 11 | 75 | 11 | 64 | 11 | 51 | 71 | 59 | 20 | 53 | 97 | 48 | 97 | 1 |
| 14 | 30 | 10 | 35 | 11 | 40 | 11 | 32 | 11 | 24 | 71 | 32 | 20 | 26 | 97 | 24 | 97 | 1 |
| 15 | 46 | 17 | 58 | 21 | 62 | 21 | 60 | 22 | 40 | 66 | 42 | 17 | 36 | 70 | 40 | 79 | 1 |
| 16 | 60 | 17 | 72 | 21 | 76 | 21 | 72 | 22 | 48 | 66 | 56 | 17 | 48 | 70 | 40 | 79 | 1 |

TABLE 3

Autoclave Data
Slicing Cam Cut Data

| Example | Autoclave Cycles | Mean (cycles) | Standard Deviation |
|---|---|---|---|
| 17 (Control) | None | 32 | 11 |
| 18 | 1 | 47 | 18 |
| 19 | 3 | 63 | 19 |
| 20 | 6 | 34 | 6 |
| 21 | 9 | 46 | 13 |
| 22 | 12 | 25 | 7 |
| 23 | 24 | 43 | 15 |

TABLE 4

Ethylene Oxide Sterilization Data
Slicing Cam Cut Data

| Example | Sterilization Cycles | Mean (cycles) | Standard Deviation |
|---|---|---|---|
| 17 (Control) | None | 32 | 11 |
| 24 | 1 | 68 | 30 |
| 25 | 3 | 49 | 14 |
| 26 | 6 | 49 | 19 |
| 27 | 9 | 38 | 11 |
| 28 | 12 | 56 | 17 |
| 29 | 24 | 52 | 14 |

TABLE 5

Sodium Hydrochlorite Treatment Data

| Example | Fabrication | Weight (g) | Thickness mm/inches | Cut Resistance Impact Cam (mean) | S.D. |
|---|---|---|---|---|---|
| 30 (Control) | Nylon | 10.3 | 1.03/0.041 | 2.89 | 1.17 |
| 31 (Comparative) | Nylon | — | — | 1.33 | 0.50 |
| 32 (Control) | Polyester | 12.8 | 0.48/0.019 | 2.56 | 1.13 |
| 33 (Comparative) | Polyester | — | — | 1.33 | 0.50 |
| 34 (Control) | Kevlar ® 29 Cont. Fil. | 10.1 | 0.45/0.018 | 30.9 | 11.1 |
| 35 | Kevlar ® 29 Cont. Fil. | — | — | 12.3 | 9.71 |
| 36 (Control) | Spectra ® 1000 | 10.2 | 0.63/0.025 | 7.33 | 4.24 |
| 37 | Spectra ® 1000 | — | — | 7.33 | 6.56 |
| 38 (Control) | Spectra ® | 11.5 | 0.95/0.038 | 16.8 | 6.06 |
| 39 | Spectra ® | — | — | 16.2 | 10.2 |

TABLE 6

| | GLOVE KNITTING PARAMETERS (C VALUES)[1] | | | | | | | |
|---|---|---|---|---|---|---|---|---|
| EXAMPLE | LITTLE | RING | MIDDLE | INDEX | PALM | THUMB | HEEL | CUFF |
| 30, 31 | 68 | 70 | 84 | 70 | 54 | 56 | 52 | 46 |
| 32, 33 | 46 | 70 | 80 | 70 | 54 | 48 | 56 | 46 |
| 34, 35 | 64 | 66 | 84 | 66 | 50 | 52 | 48 | 46 |
| 36, 37 | 64 | 66 | 84 | 66 | 50 | 52 | 48 | 46 |
| 38, 39 | 64 | 66 | 84 | 66 | 50 | 52 | 48 | 46 |

[1]W values identical to 13 gauge data of Table 2.

We claim:

1. A flexible, uncoated glove made from a layer comprising cut resistant fibrous material adhered to a surface of an elastomeric glove without being fully encapsulated thereby, said glove being characterized by: being cut resistant over some portion thereof by enduring without cutting through at least 5 cycles of an impact cam cut test; and being compliant and offering a high degree of tactility.

2. The glove of claim 1 wherein said fibrous material comprises a high molecular weight polyethylene.

3. The glove of claim 2 wherein said fibrous material comprises chopped fiber having a denier per filament of about 0.5 to about 15.

4. The glove of claim 1 further characterized by substantially retaining said cut resistance after autoclaving at temperatures of up to about 121.1° C., (250° F.) for at least about 30 minutes.

5. The glove of claim 1 wherein said fibrous material consists essentially of a chopped high molecular weight polyethylene fiber having a denier per filament of about 0.5 to about 15.

6. The glove of claim 1 wherein said fibrous material is adhered to said surface by flocking.

7. The glove of claim 1 further characterized by substantially retaining said cut resistance after sterilizing with ethylene oxide.

8. The glove of claim 1 further characterized by weighing no more than about 30 g.

9. The glove of claim 8 characterized by weighing no more than 20 g.

10. The glove of claim 1 further characterized by having a cut resistance of at least 5 cycles of an impact cam cut test after a disinfectant treatment with sodium hypochlorite.

11. The glove of claim 1 wherein said elastomeric glove comprises a latex.

12. The glove of claim 1 wherein said fibrous material comprises poly(p-phenylene terephthalamide).

13. The glove of claim 1 wherein said layer consists essentially or cut resistant fibrous material.

* * * * *

UNITED STATES PATENT AND TRADEMARK OFFICE
CERTIFICATE OF CORRECTION

PATENT NO.   : 5,568,657
DATED        : October 29, 1996
INVENTOR(S)  : CORDOVA ET AL.

It is certified that error appears in the above-identified patent and that said Letters Patent is hereby corrected as shown below:

On the title page, item

[75] Inventors: "Robert C.W. Hofer" should read --Robert C. Wincklhofer--

Signed and Sealed this

Twenty-eighth Day of January, 1997

Attest:

BRUCE LEHMAN

Attesting Officer      Commissioner of Patents and Trademarks